United States Patent
Goldfarb et al.

(10) Patent No.: US 8,840,680 B2
(45) Date of Patent: Sep. 23, 2014

(54) CONTROL SYSTEM FOR JOINTED MECHANICAL DEVICES

(75) Inventors: Michael Goldfarb, Franklin, TN (US); Skyler Ashton Dalley, Nashville, TN (US); Huseyin Atakan Varol, Astana (KZ); Tuomas Emory Wiste, Genoa (IT)

(73) Assignee: Vanderbilt University, Nashville, TN (US)

( * ) Notice: Subject to any disclaimer, the term of this patent is extended or adjusted under 35 U.S.C. 154(b) by 176 days.

(21) Appl. No.: 13/391,558

(22) PCT Filed: Aug. 20, 2010

(86) PCT No.: PCT/US2010/046054
§ 371 (c)(1),
(2), (4) Date: Feb. 21, 2012

(87) PCT Pub. No.: WO2011/022572
PCT Pub. Date: Feb. 24, 2011

(65) Prior Publication Data
US 2012/0150321 A1  Jun. 14, 2012

Related U.S. Application Data

(60) Provisional application No. 61/235,425, filed on Aug. 20, 2009.

(51) Int. Cl.
| | |
|---|---|
| A61F 2/72 | (2006.01) |
| B25J 9/12 | (2006.01) |
| B25J 9/18 | (2006.01) |
| B25J 9/16 | (2006.01) |
| B25J 15/00 | (2006.01) |
| A61F 2/58 | (2006.01) |
| A61F 2/70 | (2006.01) |
| A61F 2/76 | (2006.01) |

(52) U.S. Cl.
CPC ........... *A61F 2/72* (2013.01); *B25J 9/1612* (2013.01); *B25J 15/0009* (2013.01); *A61F 2/583* (2013.01); *A61F 2002/704* (2013.01); *A61F 2002/7615* (2013.01); *A61F 2002/7645* (2013.01)
USPC ............ 623/25; 318/568.16; 414/4; 700/253

(58) Field of Classification Search
None
See application file for complete search history.

(56) References Cited

U.S. PATENT DOCUMENTS

| 5,383,939 A | 1/1995 | James |
| 8,512,415 B2 | 8/2013 | Herr et al. |

(Continued)

FOREIGN PATENT DOCUMENTS

| EP | 1 043 003 A1 * | 10/2000 | ................ A61F 2/72 |
| EP | 1195151 | 4/2002 | |

(Continued)

OTHER PUBLICATIONS

International Search Report for PCT/US2010/046050, International Filing Date: Aug. 20, 2010., 5 Pgs.

(Continued)

*Primary Examiner* — David H Willse
(74) *Attorney, Agent, or Firm* — Novak Druce Connolly Bove + Quigg LLP; Eduardo J. Quinones

(57) ABSTRACT

Systems and methods for controlling jointed mechanical devices are is provided, where the device is controlled based on a topographic state (300) map having one or more motion axes (D1, D2) and defining a plurality of poses and a plurality of transitions in parallel with one of the motion axes, In the map, each motion axis is associated with complementary types of motion in the device and each of the transitions associated with at least two of the poses. A method includes the steps of receiving a control signal and determining a mechanical state of the device within the topographic state map. The method further includes identifying potential transitions associated with the mechanical state based on the topographic state map. The method also includes adjusting the mechanical state based on the control signal if the control signal is associated with a type of motion associated with one of the identified transitions.

27 Claims, 5 Drawing Sheets

(56) References Cited

U.S. PATENT DOCUMENTS

| | | |
|---|---|---|
| 2004/0049290 A1 | 3/2004 | Bedard |
| 2007/0123997 A1 | 5/2007 | Herr et al. |
| 2007/0219668 A1 | 9/2007 | Takahashi et al. |
| 2008/0114272 A1 | 5/2008 | Herr et al. |

FOREIGN PATENT DOCUMENTS

| | | | |
|---|---|---|---|
| EP | 1 477 277 A1 * | 11/2004 | ............ B25B 5/00 |
| WO | WO 2008/098072 | 8/2008 | |
| WO | WO 2011022569 | 2/2011 | |

OTHER PUBLICATIONS

International Search Report for PCT/US2010/046054, International Filing Date: Aug. 20, 2010, 5 Pgs.

Written Opinion for International Application No. PCT/US2010/046050, filed Aug. 20, 2010., 6 Pgs.

Written Opinion for International Application No. PCT/US2010/046054, Filing Date Aug. 20, 2010, 6 Pgs.

Akazawa et al., "Compliant Grasp in a Myoelectric Hand Prosthesis", Controlling Flexion Angle and Compliance with Electromyogram Signals, Technological Developments in Japan, IEEE Engineering in Medicine and Biology Magazine, IEEE Service Center, Pisacataway, NJ, US, vol. 24, No. 4, XP011136048, Jul. 1, 2005, pp. 48-56.

Balasubramanian et al., "Biological Stiffness Control Strategies for the Anatomically Correct Testbed (ACT) Hand", 2008 IEEE International Conference on Robotics and Automation; Pasadena, CA, USA; XP031340237, May 19, 2008, pp. 737-742.

Lee et al., "Stiffness Control of the Coupled Tendon-Driven Robot Hand", Proceedings of the International Conference on Systems, Man and Cybernetics, XP010132342, Oct. 17, 1993, pp. 710-715.

Tsujiuchi et al., "Grasp Control Using Compliance Control with Variable Stiffness Matrix", Proceedings of the 2003 IEEE/RSJ; Int'l Conference on Intelligent Robots and Systems; Las Vegas, Nevada; vol. 4; XP010671283, Oct. 27, 2003, pp. 3294-3299.

Wiste et al., "Design of a Multifunctional Anthropomorphic Prosthetic Hand with Extrinsic Actuation", 2009 IEEE 11th International Conference on Rehabilitation Robotics; Kyoto International Conference Center, Japan; XP031516352, Jun. 23, 2009, pp. 675-681.

* cited by examiner

CONTROL SYSTEM FOR JOINTED MECHANICAL DEVICES

CROSS-REFERENCE TO RELATED APPLICATIONS

This application is a §371 national stage entry of International Application No. PCT/US2010/046054, filed Aug. 20, 2010, which claims priority to U.S. Provisional Application No. 61/235,425, filed Aug. 20, 2009 both of which are hereby incorporated by reference.

FIELD OF THE INVENTION

The present invention relates to jointed mechanical devices, and more specifically to a control system for jointed mechanical devices.

BACKGROUND

Jointed mechanical devices, such as robotic prosthetic devices, for simulating and replacing natural limbs and appendages have been in use for decades. However, the design and operation of such devices generally fail to simulate an appreciable number of the discrete movements of these natural limbs and appendages. For example, hand prosthetic devices range from a passive type, which simulate the appearance of a natural hand but do not move, to newer myoelectric devices, having various combinations of pulleys, cables, linkages and the like with battery-powered operating and control systems, powered by electromyogram (EMG) signals generated by muscles in a residual limb. In general, these conventional band prosthetic devices include only a hook or cooperating digits which can grasp an object between them. As a result, they are generally incapable of doing anything else. Although the ability to grasp and hold objects can be a significant improvement for the lifestyle of a hand and/or arm amputee, such amputees are often dissatisfied with the limited utility of such prosthetic devices.

SUMMARY

Embodiments of the invention concern control systems for jointed mechanical devices. In a first embodiment of the invention, a method for controlling a jointed mechanical device is provided, where the device is controlled based on a topographic state map having one or more motion axes and defining a plurality of poses and a plurality of transitions in parallel with one of the motion axes. In the map, each of the motion axes is associated with complementary types of motion in the device and each of the plurality of transitions is associated with at least two of the plurality of poses. The method includes the steps of receiving a control signal and determining a mechanical state of the device within the topographic state map. The method further includes identifying one or more transitions of the plurality of transitions associated with the mechanical state based on the topographic state map. The method also includes adjusting the mechanical state based on the control signal if the control signal is associated with a type of motion associated with one of the one or more the identified transitions.

In a second, embodiment of the invention, a control system is provided. The control system includes a storage element for storing a topographic state map for a jointed mechanical device, the map having one or more motion axes and defining a plurality of poses for the device and a plurality of transitions in parallel with one of the motion axes, and where each of the motion axes is associated with complementary types of motion in the device and each of the plurality of transitions is associated with at least two of the plurality of poses. The control system also includes at least one interface for receiving a control signal. The control system further includes a processing element coupled to the storage element and the interface. The processing element is configured for determining a mechanical state of the device within the topographic state map, identifying one or more transitions of the plurality of transitions associated with the mechanical state based on the topographic state map, and adjusting the mechanical state based on the control signal if the control signal is associated with a type of motion associated with one of the one or more the identified transitions.

In a third embodiment of the invention, a device is provided. The device includes a base and a plurality of digits pivotably coupled to the base, where each of the plurality of digits includes a plurality of phalangeal portions connected by a plurality of flexible joint portions. The device also includes a plurality of force actuators coupled, to the plurality of digits and configured to cause motions of the plurality of digits. The device further includes a control system for adjusting an operation of the plurality of force actuators based on a mechanical state of the plurality of digits, a topographic state map, and at least one control signal. In the device, the map has one or more motion axes and defines a plurality of poses for the device and a plurality of transitions in parallel with one of the motion axes, where each of the motion axes is associated with complementary types of motion in the device, and each of the plurality of transitions is associated with at least two of the plurality of poses.

In a fourth embodiment of the invention, a prosthetic device is provided. The prosthetic device includes at least one member and a hand device coupled to the member. The hand device includes a base and a plurality of digits pivotably coupled to the base, where each of the plurality of digits includes a plurality of phalangeal portions connected by a plurality of flexible joint portions. The hand device also includes a plurality of force actuators coupled to the plurality of digits and configured to cause motions of the plurality of digits. The prosthetic device also includes a control system for adjusting an operation of the plurality of force actuators based on a mechanical state of the plurality of digits, a topographic state map, and at least one control signal. In the prosthetic device, the map has one or more motion axes and defines a plurality of poses for the device and a plurality of transitions in parallel with one of the motion axes, where each of the motion axes is associated with complementary types of motion in the device and each of the plurality of transitions is associated with at least two of the plurality of poses.

DETAILED DESCRIPTION

Figure 1:
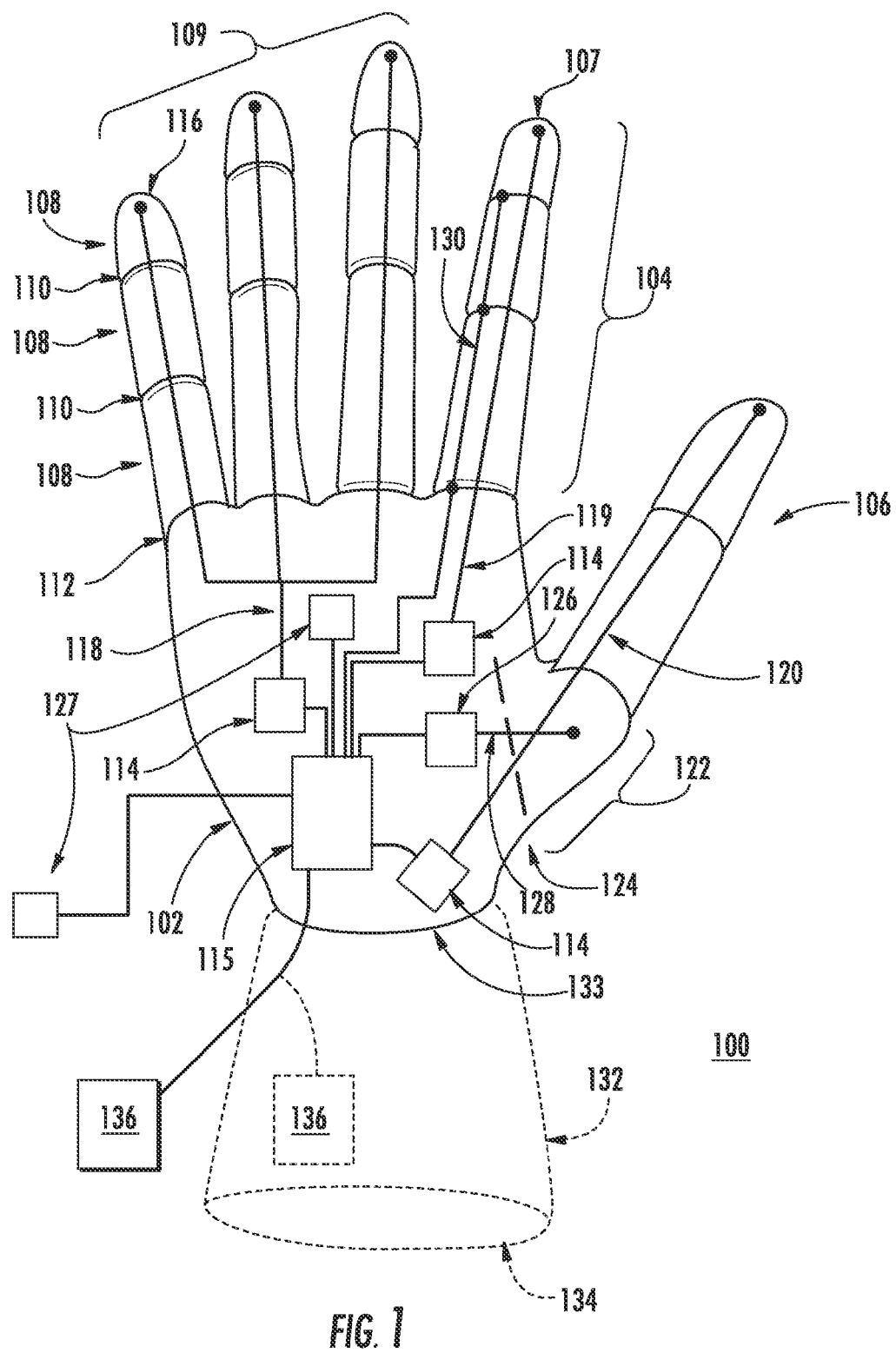
FIG. 1 is an anterior view of a prosthetic hand device in accordance with an embodiment of the invention.

The present invention is described with reference to the attached figures, wherein like reference numerals are used throughout the figures to designate similar or equivalent elements. The figures are not drawn to scale and they are provided merely to illustrate the instant invention. Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. In other instances, well-known structures or operations are not shown in detail to avoid obscuring the invention. The present invention is not limited by the illustrated ordering of acts or events, as some acts may occur in different orders and/or concurrently with other acts or events. Furthermore, not all illustrated acts or events are required to implement a methodology in accordance with the present invention.

Conventional control methods for jointed mechanical devices, particularly robotic prosthetic devices, are generally classified into one of two groups: pattern recognition methods and direct control (non-pattern recognition) methods. The term "jointed mechanical device" as used herein, refers to any powered mechanical device having one or more movable joints, including, but not limited to, robotic prosthetic and robotic non-prosthetic devices. In direct control methods, two EMG signals are generally required to actuate each joint in the device (i.e., one EMG site for each direction of motion). However, in conventional prosthetic devices, such as myoelectric prosthetic devices, the number of independent inputs available is generally limited, and consequently, direct control methods provide simultaneous control of only one or two degrees of freedom. As a result, direct control methods are generally useful in only simpler prostheses with few active joints.

In pattern recognition methods, the device is switched, between various discrete states based on a determination of the user's intent. For example, in the case of a myoelectric prosthetic device, the control system monitors multiple EMG signals from different muscle groups in the residual limb. If the control system detects a pattern in the muscle groups from the multiple EMG signals, a grasp or pose of the device associated with the detected pattern is selected. As used herein, the terms "grasp" or "pose" refer to a particular configuration of the joints in a jointed mechanical device. Based on this selected pattern, the device is reconfigured to provide the associated pose. Although such a method permits simultaneous control of a large number of joints, this method also has several drawbacks. First, the user is limited to only the grasps or poses configured by the control system. As a result, users do not have the ability to independently or directly control the joints in the device. Second, such methods are generally unreliable. In general, such EMG signals can vary over time. Accordingly, the pattern that needs to be recognized can also vary over time. As a result, additional maintenance and reprogramming of these devices is needed on a more frequent basis as compared to direct control devices.

To overcome the limitations of these conventional methods, embodiments of the invention provide a novel control methodology which allows continuous control of joints for high degree of freedom (>2) jointed mechanical devices. In the various embodiments of the invention, the actuation of joints in the device is not only based, on the input signals (e.g., an EMG signal or other control signal), but also on the current mechanical state or status of the device. The term "mechanical state" refers to the instant configuration of joints in a jointed mechanical device. That is, the user-generated direct control signals are used to drive the device between two or more pre-defined related poses. Additionally, the control is continuous, meaning that a progression from one pose to another can be halted and/or reversed at any time. As a result, the direct user control of the individual joints is provided (an advantage of direct control methods), while allowing a complex multi-joint device to be controlled with only a few control signals (an advantage of pattern recognition methods).

As described above, the various embodiments of the invention use the direct, control signals to drive a device from pose to pose. In the various embodiments of the invention, the poses and the transitions from pose to pose are pre-defined using a topographic state map. The term "topographic state map" as used herein, refers to a collection of associated poses of device, where a transition from a first pose to an adjacent or proximal pose in the topographic state map requires only a small or gradual change in the configuration of joints in the device. In the various embodiments of the invention topographic state map has one or more motion axes and defines a plurality of transitions, where each of the transitions is in parallel with one of said motion axes and each of the motion axes is associated with complementary types of motion in said device (e.g., up/down, left, right). Furthermore each of the plurality of transitions is associated with two adjacent poses.

In simpler terms, each of the transitions in the topographic state map for two or more poses are associated with a specified direction that is parallel to one of the motion axes in the topographical state map. Therefore, to transition between poses in this direction in the topographic state map, only one control input signal is needed. The result of this configuration is that instead of solving a classification problem involving all the possible poses for the device, the various embodiments of the invention only require the solution of a simpler classification problem. Particularly, a problem which only involves only the identification of the current mechanical state of the device (i.e. location within the map) and the allowable transitions from the mechanical state. Thus, only some of the transitions in the state map are allowed based on the mechanical state of the prosthesis. Once the classification problem is solved (i.e. deciding which transition within the map to proceed along), the intensity of the input control signals can then be used to generate acceleration or velocity references for the device being controlled.

Additionally, as described above, embodiments of the invention permit continuous control of the device. That is, the motion of the device can be halted anywhere between the transition between two poses. As a result, direct control over the joints involved in a transition is provided. Therefore, the user is not limited solely to a discrete set of poses defined by the topographic state map.

Although the various embodiments of the invention will be described with respect to an exemplary embodiment of a prosthetic hand device, this is for illustrative purposes only. One of ordinary skill in the art will recognize that the various embodiments of the invention can be applied to any type or configuration of jointed mechanical devices. Furthermore, although only a two dimensional topographic state map is described below, the various embodiments of the invention are not limited in this regard. One of ordinary skill in the art will recognize that a topographic state map with any number of dimensions can be used with the various embodiments of the invention.

Figure 2:
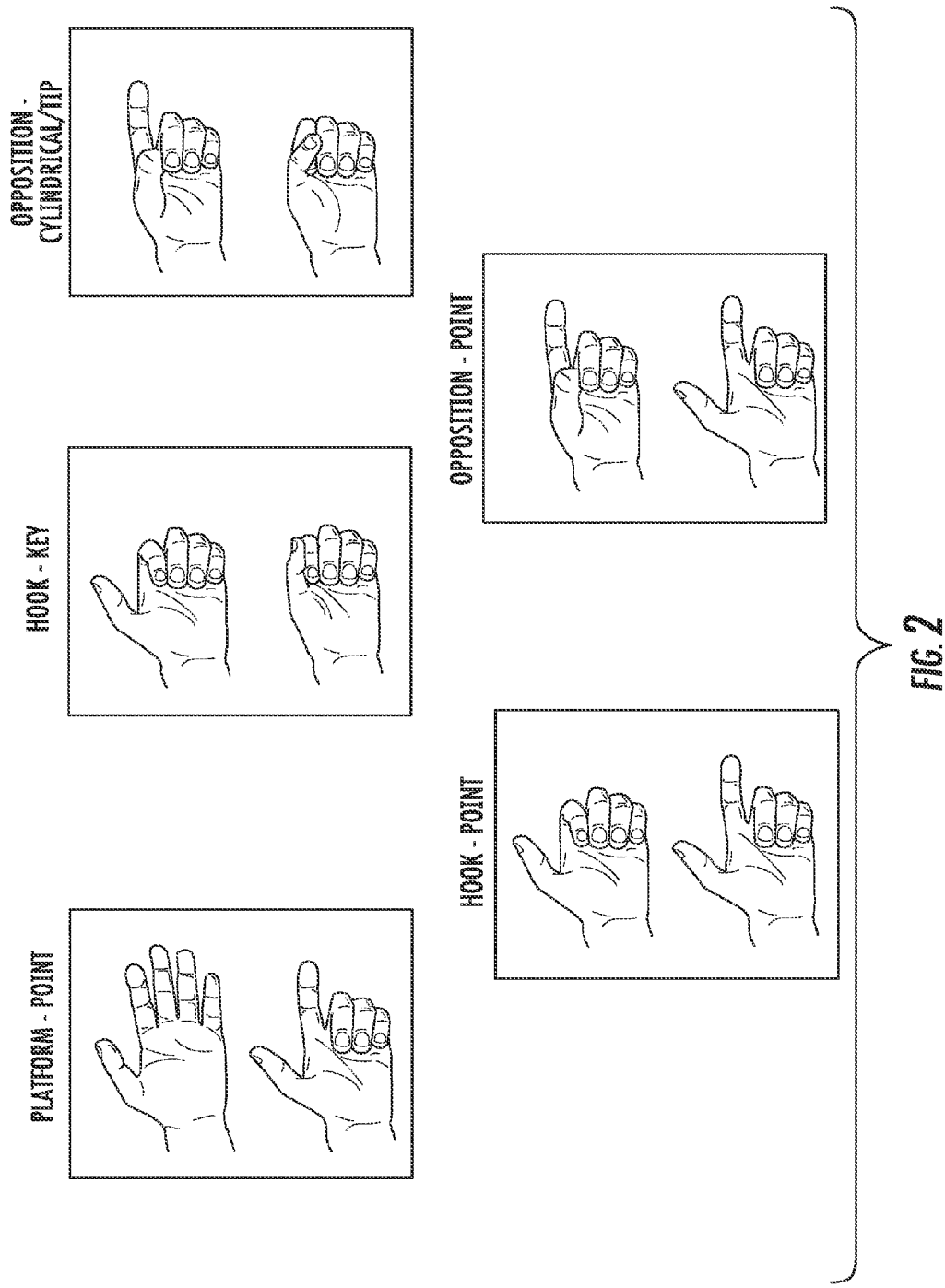
FIG. 2 shows anterior views of different poses and grasp couples for the prosthetic hand device in FIG. 1.
Figure 3:
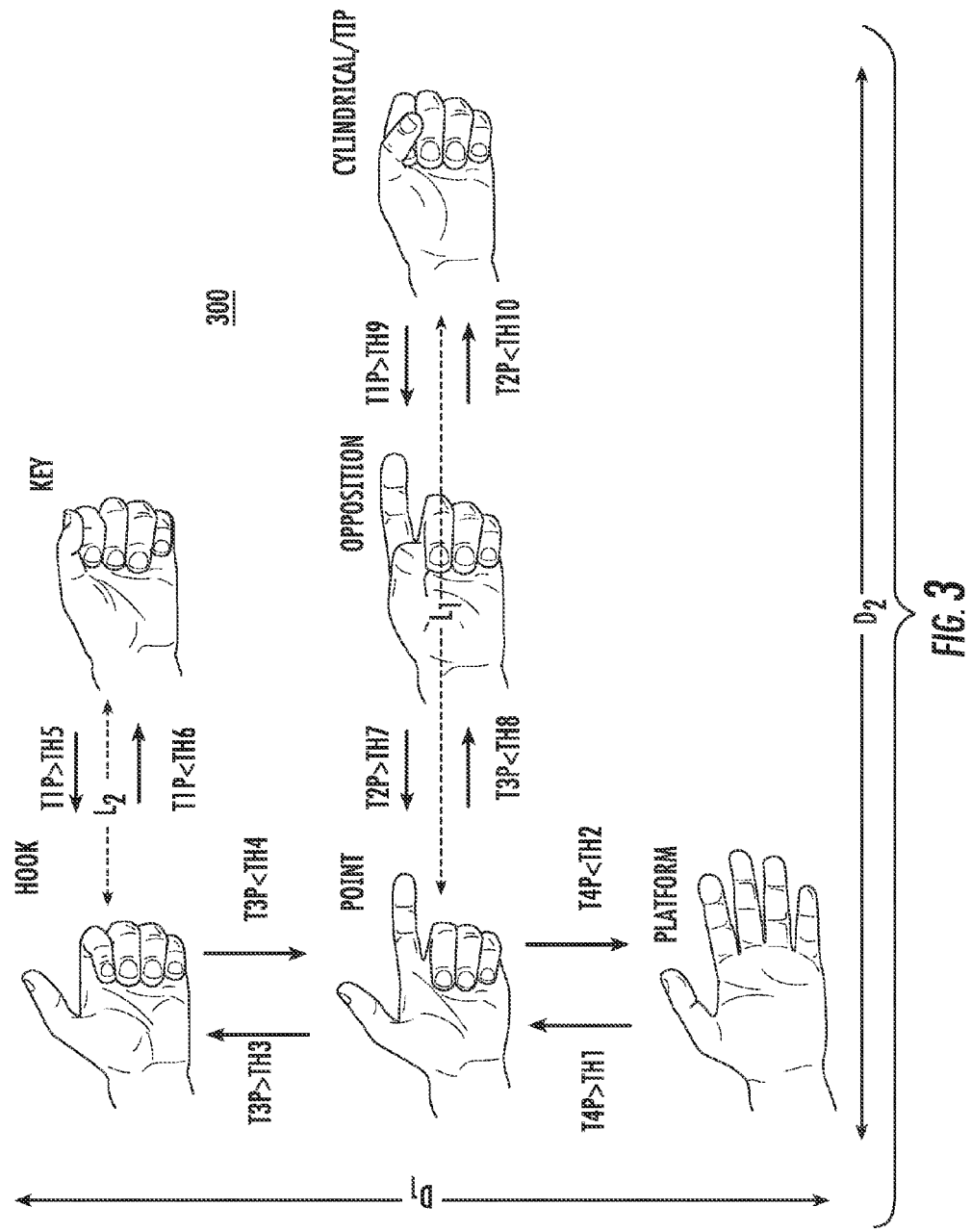
FIG. 3 shows an exemplary topographic state map in accordance with an embodiment of the invention, derived for the prosthetic hand in FIG. 1 based on the poses and grasp couples in FIG. 2.

In the various embodiments of the invention, the construction and configuration of the topographic state map can be based on the type and/or form of jointed mechanical device being used. Accordingly, the poses and the transitions can be selected to complement the range of motion and combinations of joint configurations in the device. For example, FIG. 1 shows an exemplary prosthetic hand device and FIGS. 2-3 provide one exemplary topographic state map for the hand device in FIG. 1.

FIG. 1 is an anterior view of a prosthetic hand device 100 in accordance with an embodiment of the invention. As shown in FIG. 1, the device 100 includes a base 102 and digits comprising fingers 104, a thumb 106, or any other type of flexible or deflectable element. Each of the digits in prosthetic hand device 100 includes one or more phalangeal portions 108 interconnected by flexible joint portions 110 to allow flexing or deflection of the digits in prosthetic hand device 100. An additional flexible joint portion 112 can be used to connect the digits to base 102.

In the various embodiments of the invention, the joints referenced herein refers to any type of external or integrally formed joint device or structure that is operable to provide a connection between two portions of a device and that allows movement with one or more degrees of freedom between them. Joint devices and structures can include devices in which movement is provided via a flexible material or moving components. For example, joint devices and structures can include any type of hinge device or structure.

The digits in the prosthetic hand device 100 can be actuated using one or more force actuators 114 controlled by a control system 115. The control system 115 can be coupled to one or more EMG signals to provide one or more actuation inputs to cause motion of the digits in the prosthetic hand device 100. The control system 115 can also have one or more user controls (i.e, switches, buttons, or other selection devices) or interfaces for electronically configuring its operation, as described below with respect to FIG. 5. A detailed description of the configuration and operation of the control system will be provided below with respect to FIGS. 4 and 5.

The force actuators 114 are connected the distal ends 116 of the digits of prosthetic hand device 100 via one or more actuating structures threaded through the phalangeal portions 108. The actuating structures can include cable portions 118, 119, 120 attached to a phalangeal portion 108 associated with a distal end 116 of each of the digits of prosthetic hand device 100.

In the embodiment shown in FIG. 1, the prosthetic hand device 100 is configured to provide an opposable thumb. In particular, thumb 106 can be connected to base 102 via an opposable portion 122 connected to base 102 with hinge 124. This hinged portion can also be actuated using a force actuator 126 using an actuating structure including a cable portion 128 for applying a force to the opposing portion 122 and to cause it to pivot with respect to hinge 124.

In operation, the force actuators 114 displace cables 118-120 (i.e., apply a force to cables 118-120), causing fingers 104 and thumb 106 to flex according to joints 110. Similarly, force actuator 126 displaces cable 128 (i.e., applies a force to cable 128), causing opposing portion 122 to flex according to hinge 124. Although the digits of prosthetic hand device 100 and opposing portion 122 could potentially flex in any direction, one of ordinary skill in the art would recognize that base 102, phalangeal portions 108, joints 110, opposing portion 122, and hinge 124 can be configured to allow motion in an anterior direction to approximate the motion of digits in a natural hand.

In some embodiments of the invention, the prosthetic hand device 100 is configured to include elastic elements in joints 110, 112, and hinge 124 to provide a restorative force when force on any of the cables 118-120 and 128 is relieved. The restorative force returns the digits of the hand device 100 to a resting position. For example, at each of the joints, a joint spring device, such as a torsion spring, can be used to provide the elastic component. However the various embodiments of the invention are not limited in this regard and, any type of spring device can be used to provide the joint spring devices.

In the embodiment shown in FIG. 1, one or more of the digits of prosthetic hand device 100 can be configured to operate in concert using a single force actuator 114. For example, as shown in FIG. 1, the thumb 106 and index finger 107 are each operated by cables 120 and 119, respectively. The other or non-index fingers 109 are configured to operate using cable 118. Such a configuration can generally be provided in prosthetic hand device 100 since independent motion of a thumb or an index finger is most common in gesturing and grasping in a natural hand. Furthermore, non-index fingers 109 typically operate in concert, also simulating typical motion in a natural hand. Such a configuration also permits a simpler configuration for control system 115, as the control of only two fingers and an opposing thumb motion is effectively required. However, the various embodiments of the invention are not limited in this regard and independent control of all digits in hand 100 can be provided.

In the various embodiments of the invention, the configuration of the force actuators 114 can be selected based on the configuration of the actuating structures. For example, for the actuating structures shown in FIG. 1 (cables 118-120), the force actuators 114 can comprise an electric motor and pulley assembly configured to operate with each of cables 118-120 of the actuating structures. Additionally, such a configuration can also include a roller clutch between a motor and a pulley in a force actuator 114. The roller clutch can be used to lock a cable of the actuating structure in place so that the configuration of the fingers 104, thumb 106, and or opposing portion 122 is also locked at a position when the motor is turned off. A similar configuration can be provided for force actuator 126 and cable 128.

In some embodiments of the invention, one or more sensors can be incorporated into various portions of hand device 100 for determining a mechanical state of hand device 100 directly or indirectly. For example, at least a portion of joints 110 can include sensors for generating signals indicative of a position of joints 110 to directly provide mechanical state information. These sensors can then be coupled to control system 115, as shown by connector 130 in FIG. 1. In another embodiment, each of actuators 114 and 126, already coupled to control system 115, can also include sensors for providing force and/or torque information, which can be used to derive mechanical state information.

Additionally, these sensors can be used to determine the force applied by hand device 100 in order to detect the presence of an object in hand device 100. However, the various embodiments of the invention are not limited in this regard and any number of internal and/or external sensor devices 127 can be coupled to control system 115 for purposes of detecting an object in hand device 100. In such embodiments of the invention, any type of sensor device can be used, including, but not limited to mechanical, optical, or electronic sensor devices.

In some embodiments of the invention, the hand device 100 can be a portion of a larger device, such as a prosthetic arm device. In such embodiments, the hand device 100 can be mechanically coupled to at least one member 132, as shown in FIG. 1. The member 132 can be configured to attach to a residual limb or other portion of a user's body. The member 132 can include any number of movable joints, including a movable joint at joint 133 between member 132 and hand device 100. For example, as shown in FIG. 1, the member 132 can include a socket 134 for attaching member 132 to a residual limb. However, the various embodiments of the invention are not limited in this regard and member 132 can be configured to be attached to a user's body in any other way. In some embodiments, the member 132 can include sensors 136, such as EMG electrodes. However, the invention is not limited in this regard and the sensors 136 can reside external to the member 132. The configuration of the sensors 136 can be adjusted based on the particular user or source of control signals.

Based on the type of device, the poses for the topographic state map can be selected. For example, FIG. 2 shows anterior views of different poses (platform, point, hook, key, opposition, cylindrical/tip) for hand device 100. Furthermore, FIG. 2 shows an exemplary set of grasp couples (platform to point, hook to key, opposition to cylindrical/tip, hook to point, opposition to point). In all of these grasp couples, the transitions between the different poses in the grasp couple only involve some of the fingers to change their positions while some other fingers do not move. This is tabulated below in Table 1 with respect to the hand device 100 in FIG. 1.

TABLE 1

Motions During Hand Pose Transitions

| Pose Transition | Motion required |
| --- | --- |
| Point ⟷ Platform | Non-index Fingers |
| Key ⟷ Hook | Opposing portion and/or Thumb |
| Cylindrical/Tip ⟷ Opposition | Index Finger and Opposing portion and/or Thumb |
| Point ⟷ Hook | Index Finger |
| Point ⟷ Opposition | Opposing portion and/or Thumb |

Although only a few exemplary poses and grasp couples are shown in FIG. 2, the various embodiments of the invention are not limited in this regard. Rather, in the various embodiments of the invention, any number of poses can be used, including poses between the poses listed above in Table 1 and shown in FIG. 2. Additionally, any number of sub-poses can also be defined. That is, for a particular pose, one of multiple forms of the pose can be selected based on one or more conditions, such as operating conditions or user preferences. An example of such sub-poses will be described below in greater detail with respect to the cylindrical/tip pose. Once the poses and the grasp couples have been identified or selected for a device, these can be used to construct a topographic state map. Construction of a topographic state map is described below in greater detail with respect to FIG. 3.

FIG. 3 shows an exemplary topographic state map 300 for the prosthetic hand device in FIG. 1 using the poses and grasp couples in FIG. 2. In general, the map 300 is organized to provide transitions from pose to pose based on the grasp couples identified in FIG. 2. That is, each pose can have one or more adjacent or proximal poses in the map 300, where the proximal poses correspond to the other pose in the grasp couples associated with the particular pose. As a result, each pose can have one or more proximal poses. For example, a platform pose, which is involved in only one grasp couple is only proximal to the other pose, the point pose. In contrast, the point pose, which is involved in two additional grasp couples, has a total of these proximal poses, the hook, opposition, and platform poses. The cylindrical/tip pose is also only involved in one grasp couple and is only proximal to the other pose, the opposition pose. Similarly, the key pose is also only involved in one grasp couple and is also only proximal to one pose, the hook pose.

Although the cylindrical/tip pose is shown as a single pose in FIGS. 2 and 3, this pose effectively provides two different sub-poses in some embodiments of the invention, namely a cylindrical sub-pose and a tip sub-pose. In both sub-poses, the tips of the thumb and index fingers are moved towards each other. However, whether the opposition pose transitions to the cylindrical sub-pose or the tip sub-pose is determined by whether or not an object is currently being held by a hand. If an object is present, a hand will form a cylindrical grasp around the object. That is, the thumb, the index finger, and the non-index fingers of the hand (the middle, ring, and little fingers) will wrap around the object being held. At the most, only the tips of the non-index fingers would come into contact the hand in the cylindrical grasp, if the object is small enough. If an object is not present, a hand can instead form a tip grasp. That is, the thumb and index finger meet (i.e., as to pinch) and the non-index fingers are moved into contact with the palm of the hand. Such a pose is useful for picking or holding small objects. In the various embodiments of the invention, the selection of the cylindrical or tip sub-pose can be performed in various ways. For example, in some embodiments of the invention, one or more external or internal sensors can be provided to detect the presence of an object in the hand. In another example, a switch or other selection device can be provided to manually select between the cylindrical and the tip sub-poses. However, the various embodiments of the invention are not limited in this regard and any other means of mechanically or electronically selecting between sub-poses can be used.

In addition to defining the position of the poses in map 300 with respect to each other, the poses in the topographic state map can also be arranged to reduce the number of signals required to transition between poses. In particular, the arrangements of the poses can be selected such that poses associated with particular types of movement in the hand device 300 lie along a same motion axis of the map 300. Consequently, the hand device can transition between these poses utilizing a single signal type as opposed to requiring multiple signal types or patterns for each pose. Furthermore, the directions for these poses can be selected such that the motions are more intuitive for the user. This is also conceptually illustrated in map 300 in FIG. 3.

In FIG. 3, the platform, point, and hook states are arranged to lie along a line parallel to a first motion axis $D_1$ in the topographical state map. This arrangement recognizes that to transition between these states, only the amount of index and non-index finger extension and flexion is varied. As used herein, the term "extension" refers to the straightening the joints resulting in an increase of angle (i.e., moving the base of the fingers away from the palm of the hand). The term "flexion" refers to the complement of extension, particularly to the bending of joints resulting in a decrease of angle (i.e., moving the base of the fingers toward the palm of the hand). For example, to transition from a platform pose to the point pose, flexion of the non-index fingers in hand device 100 is first performed. To further transition to a hook pose from the point pose, flexion of the index finger is performed. Afterwards, to return to the platform pose, extension of the index finger provides a transition from the hook pose to the point pose. Subsequent extension of the non-index fingers then provides a transition from the point pose to the platform pose. As a result of the relationship between these states, only a single pair of control signals, one associated with flexion and one associated with extension, would be needed to provide transitions between these poses. Furthermore, because the extension and flexion of the fingers is similar to that in a natural hand, operation of the hand device 100 is more intuitive for the user to use and learn.

Similarly, the point, opposition, and cylindrical/tip states are arranged to lie along a first line L1 in parallel to a second motion axis D2 in the topographical state map. This arrangement recognizes that to transition between these poses, primarily only the amount of thumb and index finger adduction and abduction is varied. As used herein, the term "adduction" refers to medial movement toward the axial line (i.e., movement of the thumb or index finger towards the middle finger). The term "abduction" refers to the complement of adduction, the lateral movement away from the axial line (i.e., movement of the thumb or index finger away from the middle finger). For example, to transition from a point pose to the opposition pose, adduction of the thumb is performed. In the case of hand device 100, adduction and abduction of the thumb can require actuation of cables 120 and/or 128. To further transition to a cylindrical/tip pose from the opposition pose, further adduction of the thumb and adduction of the index finger is performed. Afterwards, to return to the point pose, abduction of the index finger and thumb provides a transition from the cylindrical/tip pose to the opposition pose and additional abduction of the thumb provides a transition from the opposition pose to the point pose. In the case of index finger 107 in FIG. 1, the adduction and abduction are actually flexion and extension of the index finger 107. However, for purposes of a control system in accordance with an embodiment of the invention, it is treated as an adduction/abduction motion when operating along line L1. As a result of the relationship between these poses, only a single pair of control signals, one associated with abduction and one associated with adduction, would be needed to provide transitions between these poses. Furthermore, because the adduction and abduction of these fingers is similar to that in a natural hand, operation of the hand device 100 is more intuitive for the user.

Similarly, the hook and key poses can also be arranged to lie along a second line $L_2$, also parallel to the second motion axis $D_2$. This arrangement also recognizes that to transition between these poses, only the amount of thumb adduction and abduction is varied. Furthermore, this arrangement further recognizes that the types of motion for the first and second lines are substantially similar. That is, the motions along lines $L_1$ and $L_2$ both comprise adduction and abduction. As a result of the relationship between these poses, only a single pair of control signals, one associated with abduction and one associated with adduction, would also be needed to provide transitions between these states. Furthermore, since the $L_2$ transitions from a different pose as compared to $L_1$ (i.e., hook pose vs. point pose), the same signal can be used for transitioning between poses in both lines.

As a result, no additional control signals are required for the second line. Rather, in the various embodiments of the invention, the effect of a signal indicating adduction or abduction (i.e., whether $L_1$ or $L_2$ is selected) is based on the mechanical state of the device along the first line. Similarly, the effect of a signal indicating flexion or extension would be based on the mechanical state of the device along $L_1$ or $L_2$ line. Accordingly, map 300 provides a topographic state map for transitioning between the six states using only two pairs of control signals, one pair for flexion/extension and one pair for adduction/abduction.

Figure 4:
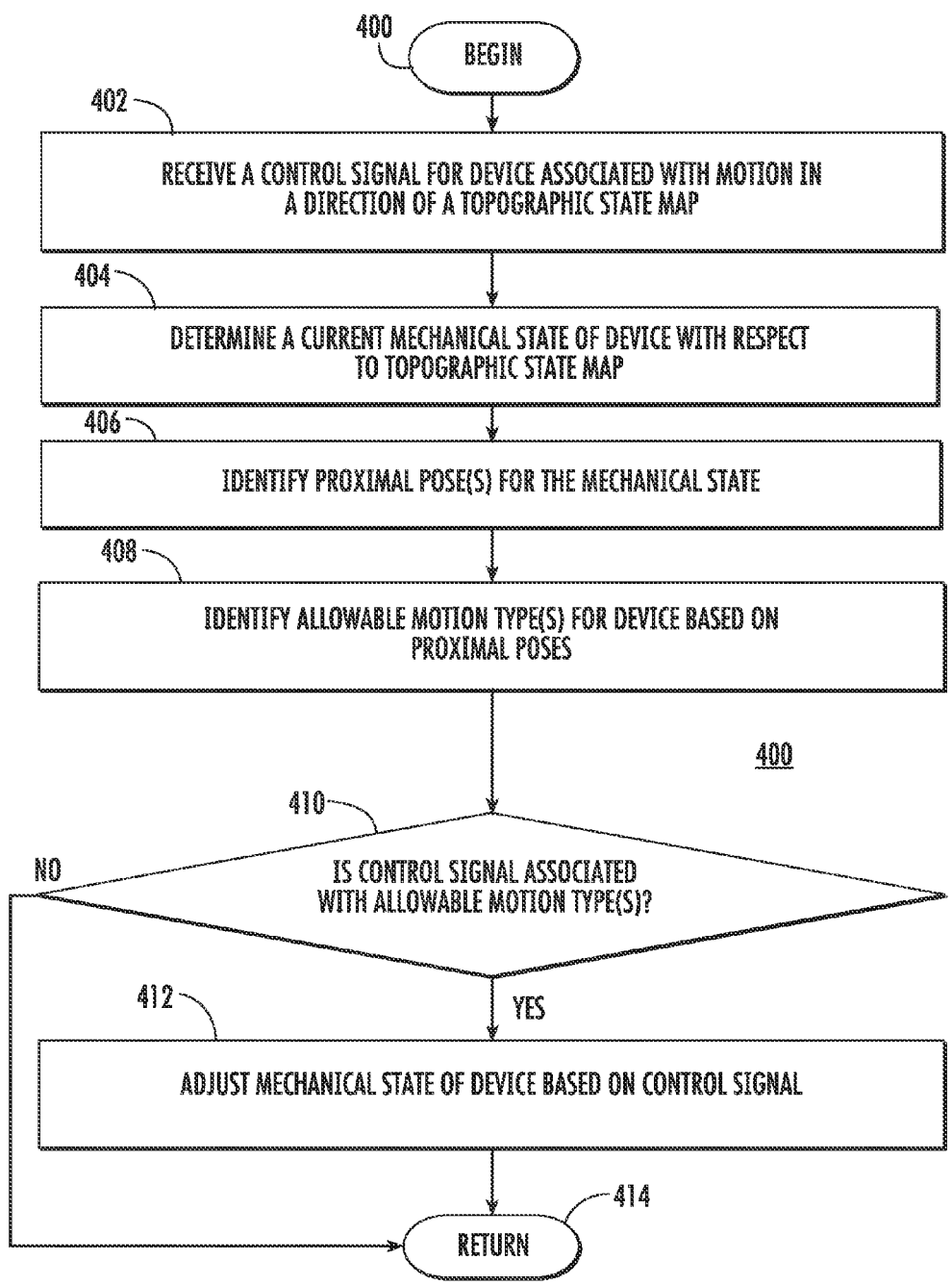
FIG. 4 shows a flow chart of steps in an exemplary method for operating a control system for a jointed mechanical device in accordance with an embodiment of the invention.

Once the topographic state map is constructed, a control system for a jointed mechanical device can be configured to use the map to control operation of the device. An exemplary method 400 for controlling such devices is shown in FIG. 4. Method 400 begins at block 400 and proceeds to block 402. At block 402, a control signal is received that is associated with motion in a particular direction in the topographic state map. For example, referring back to FIG. 3, a control signal can be received that is associated with motion in a direction parallel to one of motion axes $D_1$ or $D_2$, indicating that a user wishes to perform extension/flexion or abduction/adduction, respectively, of the digits in hand device 100.

Subsequently or concurrently with block 402, a current mechanical state of the device can be determined at block 404. In general, the current mechanical state of a device refers to the current configuration of the joints in the device. In the various embodiments of the invention, this configuration can be determined directly or indirectly, depending on the sensors available in the device. For example, some devices can include sensors at some or each of the joints, sensors at all or some of the force actuators, or any combination thereof. One of ordinary skill in the art will recognize that since continuous control is provided in the various embodiments of the invention, in many cases the mechanical state of the device may not correspond to one of the poses. That is, a current configuration of the device may be a configuration of joints falling between two of the poses.

Once the mechanical state of the device is determined at block 404, the proximal poses for the mechanical state can be determined. For example, if a current mechanical state corresponds to a joint configuration between two of the poses, the proximal poses comprises these two poses. If a current mechanical state corresponds to a joint configuration matches one of the poses, the proximal poses comprises the poses associated with the grasp couples for the matching pose. In some embodiments, the amount of matching between a mechanical state and a pose can be varied to increase usability of the device. For example, referring back to FIG. 3, rather than requiring that a mechanical state exactly match the point pose to begin transitioning along line $L_1$, a matching can be said to occur if the current mechanical state substantially matches the pose. The amount of matching can be adjusted according to a variety of factors, including user control ability, tasks to be performed by the user, and the proximal poses. Therefore, a match could be recognized by the control system if the current state of the hand device is within match value, such as 5%, 10%, or 20% of the nearest proximal pose (e.g., by the amount of distance of motion remaining), associated with $L_1$ or $L_2$. However, the various embodiments of the invention are not limited in this regard and any value could be used. Therefore, if a pose is currently with a match value, providing a signal associated with a different motion axis can be configured to trigger the pose to move to the associated proximal pose and begin motion along the different motion axis. In some case, the device can be configured to require the amplitude or time of such a signal to meet at least a threshold amount to begin such motions.

After the proximal poses for the mechanical state are identified at block 406, the types of motion allowable from the current mechanical state (i.e., the allowable transitions in the topographic state map) can be identified at block 408. Although the topographic state map allows for different types of motions, in some instances, the types of motion may be limited to one or two. For example, referring to FIG. 3, if a mechanical state corresponds to the platform pose, only flexion is permitted. Similarly, at the cylindrical/tip or key poses, only abduction is permitted. In other cases, only motion along one motion axis is permitted. For example, if the mechanical state is at any point between the point pose and the cylindrical/tip pose, only adduction or abduction may be permitted in the topographical state map. However, in some cases, more motion is permitted. For example, at the point state, flexion, extension, and adduction (i.e. motion along both motion axes $D_1$ and $D_2$) are all permitted.

Once the allowable types of motion are identified at block 408, it is determined at block 410 whether or not the control signal corresponds to one of the allowable motions. If the control signal corresponds to one of the allowable motions at block 410, the mechanical state of the device is adjusted based on the control signals at block 412 and method 400 resumes previous processing at block 414, including repeating method 400 for other control signals. If the control signal does not correspond to one of the allowable motions at block 410, no change in the mechanical state of the device is provided and method 400 resumes previous processing at block 414, including repeating method 400 for other control signals.

The adjustment at block 412 can be performed in several ways. For example, in some embodiments, any amplitude or amount of signal can be used to trigger motion. However, in other embodiments, a threshold level can be provided to ensure that spurious signals or accidentally generated signals do not trigger motion. For example, in one embodiment, the threshold level can specify a minimum amplitude for the control signal can be required to trigger motion. In another embodiment, the threshold level can specify a minimum length of time of the control signal can be required. In yet other embodiments, a combination of time and amplitude threshold levels can be used.

In some embodiments, the threshold levels can be specified on a directional basis. That is, to cause motion in a direction, only a single threshold value is needed for the direction, irrespective of the mechanical state. However, in some embodiments, finer control of the transitions between poses may be desired. In such embodiments, as shown in FIG. 3, pose by pose threshold values (THi, where, i=1, 2, . . . 10) can be defined. Furthermore, as shown in FIG. 3, the threshold values need not be symmetric for different types of motion along a same direction or between proximal poses. Such a configuration allows the transitions to be further customized for particular transitions or for particular users.

In some embodiments the control system can also be configured to trigger an automatic transition to a pose. For example, in one embodiment of the invention, two threshold values for a same direction along a motion axis can be provided for a same transition. The first threshold value can be provided to allow continuous control of the transition. That is, the motion proceeds as long as the input control signal meets the threshold level. The second threshold value can be used to trigger a complete transition to the next pose. Such a configuration can be advantageous as it can allow a user to transition between multiple states using less signals and less effort.

Figure 5:
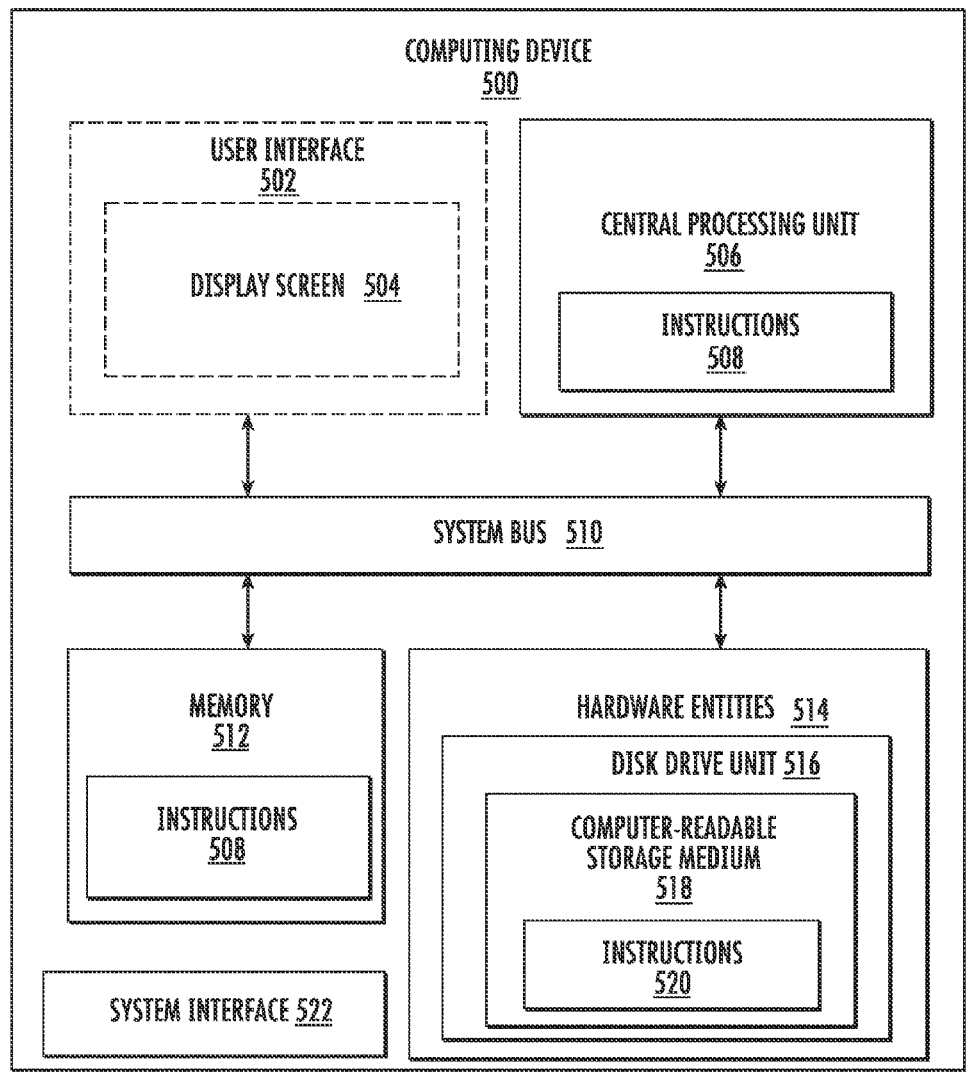
FIG. 5 is block diagram of a computing device which can be implemented as control system in accordance with an embodiment of the invention.

Referring now to FIG. 5, there is provided a detailed block diagram of a computing device 500 which can be implemented as a control system in accordance with an embodiment of the invention. Although various components are shown in FIG. 5, the computing device 500 may include more or less components than those shown in FIG. 5. However, the components shown are sufficient to disclose an illustrative embodiment of the invention. The hardware architecture of FIG. 5 represents only one embodiment of a representative computing device for controlling a jointed mechanical device.

As shown in FIG. 5, computing device 500 includes a system interface 522, a Central Processing Unit (CPU) 506, a system bus 510, a memory 512 connected to and accessible by other portions of computing device 500 through system bus 510, and hardware entities 514 connected to system bus 510. At least some of the hardware entities 514 perform actions involving access to and use of memory 512, which may be any type of volatile or non-volatile memory devices. Such memory can include, for example, magnetic, optical, or semiconductor based memory devices. However the various embodiments of the invention are not limited in this regard.

In some embodiments, computing system can include a user interface 502. User interface 510 can be an internal or external component of computing device 500. User interface 502 can include input devices, output devices, and software routines configured to allow a user to interact with and control software applications installed on the computing device 500. Such input and output devices include, but are not limited to, a display screen 504, a speaker (not shown), a keypad (not shown), a directional pad (not shown), a directional knob (not shown), and a microphone (not shown). As such, user interface 502 can facilitate a user-software interaction for launching software development applications and other types of applications installed on the computing device 500.

System interface 522 allows the computing device 500 to communicate directly or indirectly with the other devices, such as an external user interface or other computing devices. Additionally, computing device can include hardware entities 514, such as microprocessors, application specific integrated circuits (ASICs), and other hardware. As shown in FIG. 5, the hardware entities 514 can also include a removable memory unit 516 comprising a computer-readable storage medium 518 on which is stored one or more sets of instructions 520 (e.g., software code) configured to implement one or more of the methodologies, procedures, or functions described herein. The instructions 520 can also reside, completely or at least partially, within the memory 512 and/or within the CPU 506 during execution thereof by the computing device 500. The memory 512 and the CPU 506 also can constitute machine-readable media.

While the computer-readable storage medium 518 is shown in an exemplary embodiment to be a single storage medium, the term "computer-readable storage medium" should be taken to include a single medium or multiple media (e.g., a centralized or distributed database, and/or associated caches and servers) that store the one or more sets of instructions. The term "computer-readable storage medium" shall also be taken to include any medium that is capable of storing, encoding or carrying a set of instructions for execution by the machine and that cause the machine to perform any one or more of the methodologies of the present disclosure.

The term "computer-readable storage medium" shall accordingly be taken to include, but not be limited to, solid-state memories (such as a memory card or other package that houses one or more read-only (non-volatile) memories, random access memories, or other re-writable (volatile) memories), magneto-optical or optical medium (such as a disk or tape). Accordingly, the disclosure is considered to include any one or more of a computer-readable storage medium or a distribution medium, as listed herein and to include recognized equivalents and successor media, in which the software implementations herein are stored.

System interface 522 can include a network interface unit configured to facilitate communications over a communications network with one or more external devices. Accordingly, a network interface unit can be provided for use with various communication protocols including the IP protocol. Network interface unit can include, but is not limited to, a transceiver, a transceiving device, and a network interface card (NIC).

Applicants present certain theoretical aspects above that are believed to be accurate that appear to explain observations made regarding embodiments of the invention. However, embodiments of the invention may be practiced without the theoretical aspects presented. Moreover, the theoretical aspects are presented with the understanding that Applicants do not seek to be bound by the theory presented.

While various embodiments of the present invention have been described above, it should be understood that they have been presented by way of example only, and not limitation. Numerous changes to the disclosed embodiments can be made in accordance with the disclosure herein without departing from the spirit or scope of the invention. Thus, the breadth and scope of the present invention should not be limited by any of the above described embodiments. Rather, the scope of the invention should be defined in accordance with the following claims and their equivalents.

Although the invention has been illustrated and described with respect to one or more implementations, equivalent alterations and modifications will occur to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application.

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

What is claimed is:

1. A method for controlling a device comprising a plurality of joints, the method comprising:
   receiving a control signal;
   determining a mechanical state of the device within a topographic state map for the device specifying one or more motion axes, a plurality of poses for the plurality of joints, and a plurality of transitions between the plurality of poses, each of said plurality of transitions associated with one of said motion axes, each one of said motion axes associated with complementary control signals, each direction along said one of said motion axes associated with a different one of said complementary control signals, and each of said plurality of poses being a different pre-defined arrangement of said plurality of joints;
   identifying one or more transitions of said plurality of transitions associated with said mechanical state based on the topographic state map;
   determining whether the control signal is one of the complementary control signals for a one of the motion axes associated with one of the identified transitions; and
   upon determining that the control signal is a one of the complementary control signals for a one of said motion axes associated with one of said identified transitions, adjusting said mechanical state according to the one of the identified transitions in a direction associated with said one of said complementary control signals.

2. The method of claim 1, wherein said receiving further comprises detecting at least one electromyogram (EMG) control signal using one or more sensors coupled to said device.

3. The method of claim 1, wherein said determining further comprises:
   ascertaining said mechanical state based on at least one of a position of joints in said device, at least one actuator force in said device, and at least one torque measurement in said device.

4. The method of claim 1, wherein said identifying further comprises:
   determining proximal ones of said plurality of poses for said mechanical state; and
   selecting said plurality of transitions associated with said proximal ones of said plurality of poses and said mechanical state as defining said identified transitions.

5. The method of claim 1, wherein said adjusting further comprises:
   comparing at least one signal value of said control signal to at least one first threshold level associated with said one of said identified transitions;
   initiating said adjusting only if said signal value is greater than or equal to said first threshold level.

6. The method of claim 5, wherein said adjusting further comprises:
   at least partially transitioning said mechanical state to at least a proximal one of said plurality of poses in said direction associated with said control signal.

7. The method of claim 5, wherein said signal value comprises at least one of an amplitude of said control signal and a time length of said control signal.

8. The method of claim 5, wherein said adjusting further comprises:
   comparing said signal value to at least one second threshold level associated with said one of said one of said identified transitions;
   if said signal value is greater than or equal to said second threshold level, altering said mechanical state to substantially match a proximal pose in said topographic state map associated with said one of said identified transitions regardless of the duration of the control signal.

9. A control system, comprising:
   a storage element for storing a topographic state map for a jointed mechanical device comprising a plurality of joints, said map specifying one or more motion axes, a plurality of poses for said plurality of joints, and a plurality of transitions between the plurality of poses, each one of said motion axes associated with complementary control signals, each direction along said one of said motion axes associated with a different one of said complementary control signals, and each of said plurality of poses being a different pre-defined arrangement of said plurality of joints, at least one interface for receiving a control signal; and a processing element coupled to said storage element and said interface, said processing element configured for:

determining a mechanical state of the device within the topographic state map;

identifying one or more transitions of said plurality of transitions associated with said mechanical state based on the topographic state map;

determining whether the control signal is one of the complementary control signals for a one of the motion axes associated with one of the identified transitions; and determining that the control signal is a one of the complementary control signals for a one of said motion axes associated with one of said identified transitions, adjusting said mechanical state according to the one of the identified transitions in a direction associated with said one of said complementary control signals.

10. The control system of claim 9, wherein said receiving further comprises detecting at least one electromyogram (EMG) control signal using one or more sensors coupled to said interface.

11. The control system of claim 9, further comprising at least one device sensor coupled to said interface, and wherein said processing element is further during said determining for:

ascertaining said mechanical state based on a sensor signal from said sensor, said sensor signal describing at least one of a position of joints in said device, at least one actuator force in said device, and at least one torque measurement in said device.

12. The control system of claim 9, wherein said processing element is further configured during said identifying for:

determining proximal ones of said plurality of poses for said mechanical state; and selecting said plurality of transitions associated with said proximal ones of said plurality of poses and said mechanical state as defining said identified transitions.

13. The control system of claim 12, wherein said processing element is further configured during altering for:

at least partially transitioning said mechanical state to at least a proximal one of said poses in said direction associated with said one of said identified transitions.

14. The control system of claim 9, wherein said processing element is further configured during said adjusting for:

comparing at least one signal value of said control signal to at least one first threshold level associated with said one of said identified transitions;

initiating said adjusting only if said signal value is greater than or equal to said first threshold level.

15. The control system of claim 14, wherein said signal value comprises at least one of an amplitude of said control signal and a time length of said control signal.

16. The control system of claim 14, wherein said processing element is further configured during said adjusting for:

comparing said signal value to at least one second threshold level associated with said one of said one of said identified transitions;

if said signal value is greater than or equal to said second threshold level, altering said mechanical state to substantially match a proximal pose in said topographic state map associated with said one of said identified transitions regardless of the duration of the control signal.

17. A device, comprising:

a base;

a plurality of digits pivotably coupled to said base, each of said plurality of digits comprising a plurality of phalangeal portions connected by a plurality of flexible joint portions;

a plurality of force actuators coupled to said plurality of digits and configured to cause motions of said plurality of digits; and a control system for adjusting an operation of said plurality of force actuators based on a mechanical state of said plurality of digits, a topographic state map, and at least one control signal, said map specifying one or more motion axes, a plurality of poses for said device, and a plurality of transitions between the plurality of poses, each of said plurality of transitions associated with one of said motion axes, each of said motion axes associated with complementary control signals, each direction along one of said motion axes associated with a different one of said complementary control signals, and each of said plurality of poses comprising a different pre-defined arrangement for said plurality of digits.

18. The device of claim 17, further comprising a plurality of myoelectric sensors for generating said control signal, said control signal comprising at least one electromyogram (EMG) control signal.

19. The device of claim 17, further comprising at least one device sensor coupled to said control system, and wherein said control system is configured for:

ascertaining said mechanical state based on a sensor signal from said sensor, said sensor signal describing at least one of a position of joints in said device, at least one actuator force in said device, and at least one torque measurement in said device.

20. The device of claim 17, wherein said control system further comprises:

a storage element for storing said topographic state map;

at least one interface for receiving a control signal; and a processing element coupled to said storage element and said interface, said processing element configured for:

determining a mechanical state of the device within the topographic state map;

identifying one or more transitions of said plurality of transitions associated with said mechanical state based on the topographic state map; and if the control signal is associated with a type of motion associated with one of said one or more said identified transitions, adjusting said mechanical state based on said control signal.

21. The device of claim 20, wherein said processing element is further configured for during said identifying for:

determining proximal ones of said plurality of poses for said mechanical state; and selecting said plurality of transitions associated with said proximal ones of said plurality of poses and said mechanical state as defining said identified transitions.

22. The device of claim 20, wherein said processing element is further configured for during said adjusting for:

comparing at least one signal value of said control signal to at least one first threshold level associated with said one of said identified transitions;

if said signal value is greater than or equal to said first threshold level, altering said mechanical state according based on said control signal and a direction in said map associated with said one of said identified transitions.

23. The device of claim 22, wherein said signal value comprises at least one of an amplitude of said control signal and a time length of said control signal.

24. The method of claim 22, wherein said processing element is further configured for during said adjusting for:
comparing said signal value to at least one second threshold level associated with said one of said identified transitions;
if said signal value is greater than or equal to said second threshold level, altering said mechanical state to substantially match a proximal pose in said topographic state map associated with said one of said identified transitions.

25. A prosthetic device, comprising:
at least one member;
a hand device coupled to the member, said hand device comprising a base, a plurality of digits pivotably coupled to said base, each of said plurality of digits comprising a plurality of phalangeal portions connected by a plurality of flexible joint portions, and a plurality of force actuators coupled to said plurality of digits and configured to cause motions of said plurality of digits; and
a control system for adjusting an operation of said plurality of force actuators based on a mechanical state of said plurality of digits, a topographic state map, and at least one control signal, said map specifying one or more motion axes, a plurality of poses for said device, and a plurality of transitions between the plurality of poses, each of said plurality of transitions associated with one of said motion axes, each of said motion axes associated with complementary control signals, each direction along one of said motion axes associated with a different one of said complementary control signals, and each of said plurality of poses comprising a different pre-defined arrangement for said plurality of digits.

26. The prosthetic device of claim 25, wherein said member is attachable to at least one residual limb.

27. The prosthetic device of claim 26, further comprising a plurality of electromyogram (EMG) sensors for generating said control signal based on EMG signals from said residual limb.

* * * * *